(12) United States Patent
Cresina et al.

(10) Patent No.: US 7,749,224 B2
(45) Date of Patent: *Jul. 6, 2010

(54) FOOT PLATE FIXATION

(75) Inventors: Jeffery Cresina, Middlesex, NJ (US); Stephen Walulik, Phillipsburg, NJ (US)

(73) Assignee: EBI, LLC, Parsippany, NJ (US)

( * ) Notice: Subject to any disclaimer, the term of this patent is extended or adjusted under 35 U.S.C. 154(b) by 779 days.

This patent is subject to a terminal disclaimer.

(21) Appl. No.: 11/567,788

(22) Filed: Dec. 7, 2006

(65) Prior Publication Data

US 2007/0161984 A1 Jul. 12, 2007

Related U.S. Application Data

(63) Continuation-in-part of application No. 11/297,745, filed on Dec. 8, 2005, now Pat. No. 7,422,593.

(51) Int. Cl.
*A61B 17/00* (2006.01)
*A61F 4/00* (2006.01)

(52) U.S. Cl. .............................. 606/54; 606/57; 606/59

(58) Field of Classification Search .............. 606/54–59
See application file for complete search history.

(56) References Cited

U.S. PATENT DOCUMENTS

| | | | |
|---|---|---|---|
| 2,238,870 A | 4/1941 | Haynes | |
| 3,086,522 A | 4/1963 | Frohmader | |
| 3,941,123 A | 3/1976 | Volkov et al. | |
| 4,308,863 A | 1/1982 | Fischer | |
| 4,365,624 A * | 12/1982 | Jaquet | 606/56 |
| RE31,809 E | 1/1985 | Danieletto et al. | |
| 4,535,763 A | 8/1985 | Jaquet et al. | |
| 4,621,627 A | 11/1986 | DeBastiani et al. | |
| 4,696,293 A * | 9/1987 | Ciullo | 606/57 |
| 5,087,258 A * | 2/1992 | Schewior | 606/56 |
| 5,144,943 A | 9/1992 | Luttrell et al. | |
| 5,320,622 A | 6/1994 | Faccioli et al. | |
| 5,788,695 A | 8/1998 | Richardson et al. | |
| 6,036,691 A | 3/2000 | Richardson et al. | |
| 6,176,860 B1 * | 1/2001 | Howard | 606/54 |
| 6,355,037 B1 | 3/2002 | Crosslin et al. | |
| 6,840,939 B2 | 1/2005 | Venturini et al. | |
| 6,964,663 B2 | 11/2005 | Grant et al. | |
| 2007/0161984 A1 | 7/2007 | Cresina et al. | |

FOREIGN PATENT DOCUMENTS

| | | |
|---|---|---|
| FR | 2805147 | 8/2001 |
| WO | WO-9735527 | 10/1997 |
| WO | WO-03068082 | 8/2003 |

* cited by examiner

*Primary Examiner*—Pedro Philogene
(74) *Attorney, Agent, or Firm*—Harness, Dickey

(57) ABSTRACT

An external fixation system for a joint having a first and second bone and defining an anatomical axis of rotation is provided. The fixation system can include a proximal frame couplable to the first bone and a distal frame couplable to the second bone. A first connector can include a first member pivotally coupled to a second member at a first pivot axis. A second connector can include a third member pivotally coupled to a fourth member at a second pivot axis. The first and second connectors are mountable between the proximal and distal frames at a location such that the first and second pivot axes are coaxial with the anatomical axis of rotation.

22 Claims, 6 Drawing Sheets

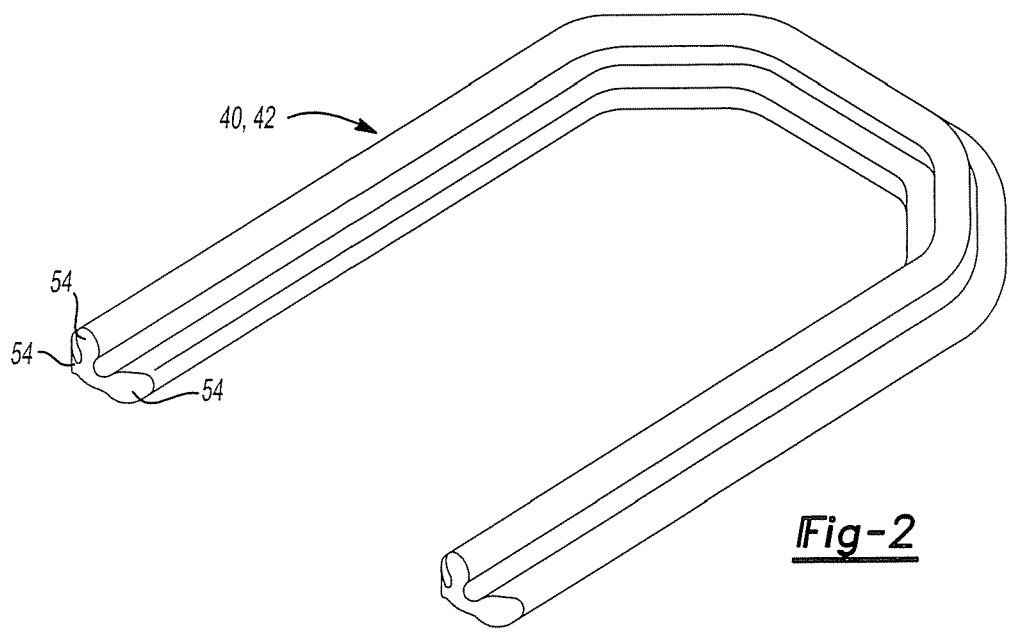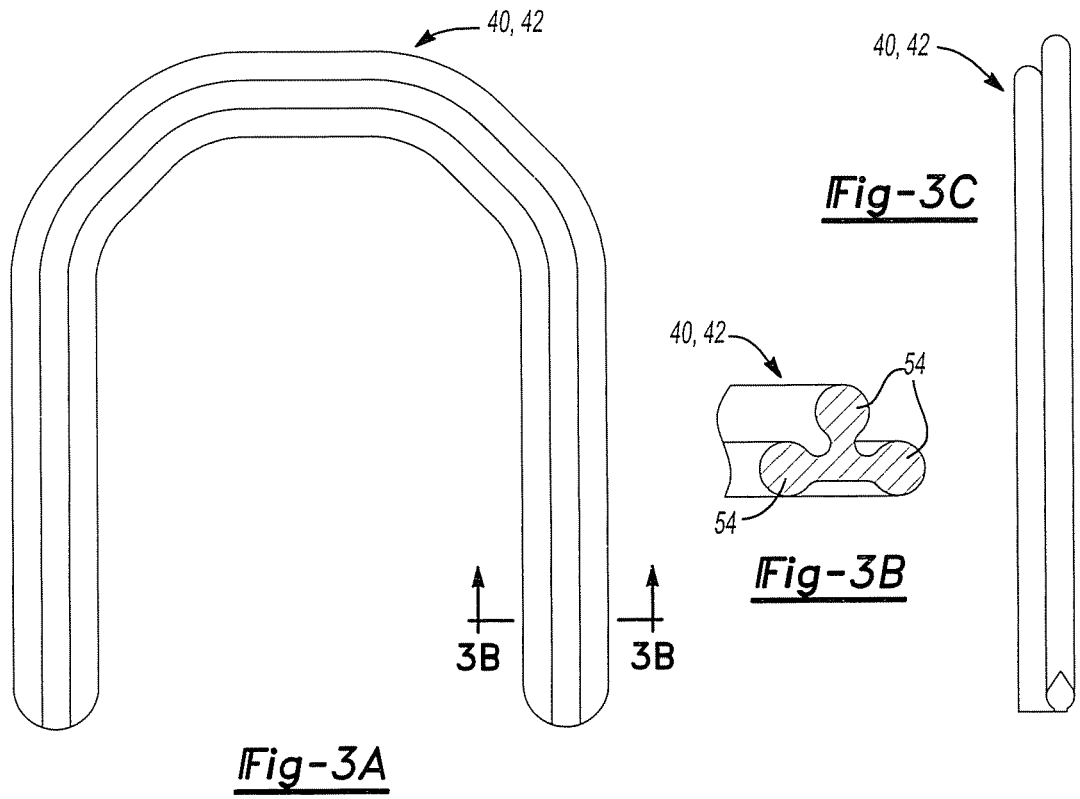

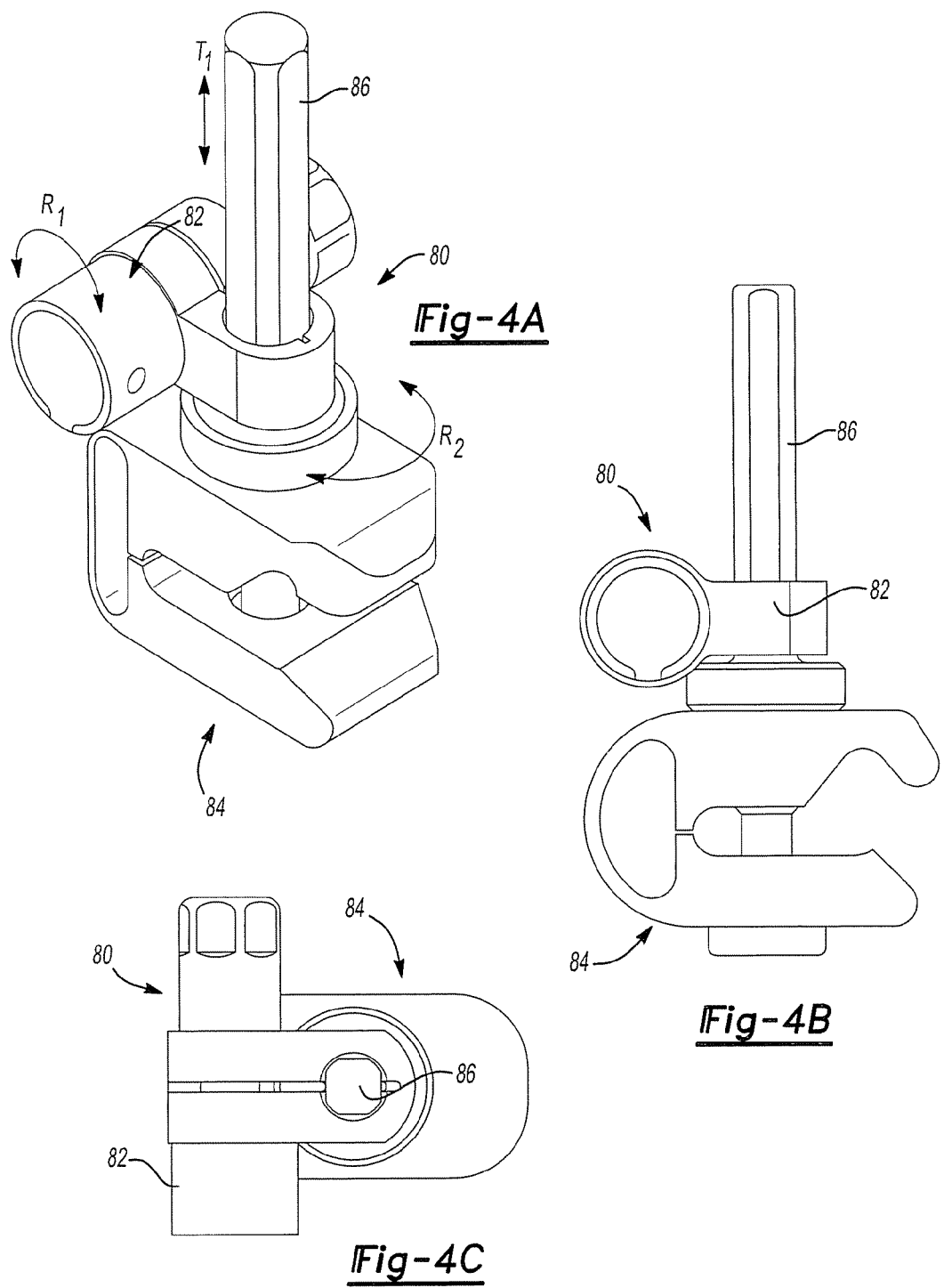

FOOT PLATE FIXATION

CROSS-REFERENCE TO RELATED APPLICATIONS

This application is a continuation-in-part of U.S. patent application Ser. No. 11/297,745 filed on Dec. 8, 2005. The disclosure of the above application is incorporated herein by reference.

INTRODUCTION

Various external fixation systems are available for addressing fractures of various bones, including the distal tibia and the foot, and for arthrodesis, deformity correction or other foot management. Some of the existing fixation systems allow radiographic examination of the fracture site. In some systems, telescopic rod connectors attached at predetermined locations provide load across the fracture site.

Although the existing external fixation systems can be satisfactory for their intended purposes, there is still a need for external fixation systems that are versatile, easily customizable, and able to address distal tibia and foot fracture and fusion conditions.

SUMMARY

The present teachings provide an external fixation system for a joint having a first and second bone and defining an anatomical axis of rotation. The fixation system can include a proximal frame couplable to the first bone and a distal frame couplable to the second bone. A first connector can include a first member pivotally coupled to a second member at a first pivot axis. A second connector can include a third member pivotally coupled to a fourth member at a second pivot axis. The first and second connectors are mountable between the proximal and distal frames at a location such that the first and second pivot axes are coaxial with the anatomical axis of rotation.

According to additional features, at least one of the first and second connectors can be adjustably secured at a plurality of locations between the proximal and distal frames. At least one of the first and second connectors can be adjustable in a direction toward and away from the proximal frame. At least one of the first and second connectors can be adjustable in a direction lateral to the proximal frame.

According to other features, the first and second members can be pivotally coupled at a ball and socket. The first member can be adapted to pivot relative to the second member through about 60 degrees of motion. The first connector can include a ring movable between a locked position wherein the ball is fixed relative to the socket and an unlocked position wherein the ball is free to rotate within the socket. The ring can be threadably connected to the socket. The first connector can include a first clamp configured for snap-on attachment at any position along at least one of the proximal and distal frames.

A method for external fixation of a joint having a first bone and a second bone and an anatomical axis of rotation is provided. A first and a second connecting member having a first and a second pivot joint are provided. A proximal frame is attached to the first bone. A distal frame is attached to the second bone. The first connecting member is attached to at least one of the proximal and distal frames such that the first pivot joint is positioned at a first location on the anatomical axis. The second connecting member is attached to at least one of the proximal and distal frames such that the second pivot joint is positioned at a second location on the anatomical axis such that the joint is located intermediate the first and second location.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present teachings will become more fully understood from the detailed description and the accompanying drawings, wherein:

FIG. 2 is a perspective view of a frame for external fixation system according to the present teachings;

FIG. 3A is a plan view of the frame of FIG. 2;

FIG. 3B is a cross-sectional view of the frame of FIG. 3A taken along axis 3B-3B;

FIG. 3C is a side view of the frame of FIG. 3A;

FIGS. 4A, 4B, and 4C are perspective, side and plan views, respectively, of a clamping assembly according to the present teachings;

DESCRIPTION OF EXEMPLARY EMBODIMENTS

The following description is merely exemplary in nature and is in no way intended to limit the disclosure, its application, or uses. For example, although the present teachings are illustrated for applications addressing fractures and/or deformities in the distal tibia and or various parts of the foot, the present teachings can be used for external fixation of other bones.

Figure 1:
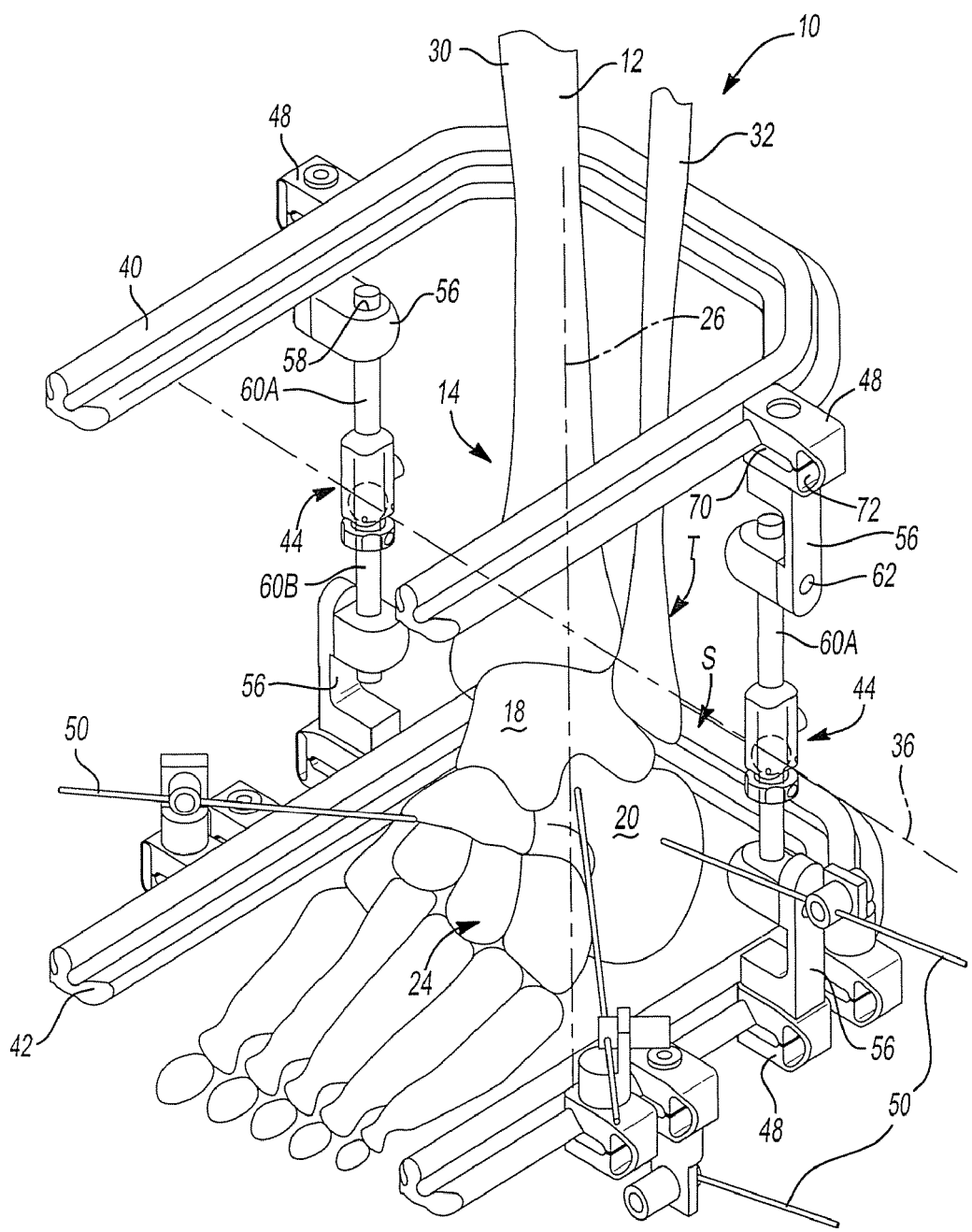
FIG. 1 is a perspective view of an external fixation system according to the present teachings, the external fixation system operatively attached to a foot.

Referring to FIG. 1, an exemplary external fixation system 10 according to the present teachings is illustrated in an environmental view for fixation of various bones or bone portions 12. As illustrated, the particular example includes fixation of various bones of an ankle 14. Prior to further discussion of the external fixation system 10, a brief description of the ankle 14 is warranted. As is known, the ankle 14 generally includes two joints, the subtalar joint S and the true ankle joint T. The subtalar joint S includes the talus 18 and the calcaneus 20 located inferiorly of the talus 18. In general, the subtalar joint S allows motion of the foot 24 about a superior/inferior axis 26 through the subtalar joint S. The true ankle joint T includes the tibia 30, the fibula 32 and the talus 18. In general, the true ankle joint T allows up and down motion of the foot 24 about a medial/lateral axis 36 defined through the true ankle joint T. The following discussion is directed to a fixation system that can selectively permit motion of the foot 24 about the medial/lateral axis 36 through the true ankle joint T. It is appreciated however, that the fixation system 10 may similarly be adapted for use with other joints defining other axes.

The fixation system 10 can include a proximal frame 40 and a distal frame 42, which can be positioned on opposite sides of a fracture/fusion site of the bone 12. The proximal and distal frames 40, 42 can be connected to each other by one or more frame connectors 44, which can be selected from various configurations. Various clamps 48 can be used with the frame connectors 44 or independently of the frame connectors 44 for attaching bone pins or wires 50, and/or rods, bars, or other fixation devices, as desirable for a particular fixation. The proximal and distal frames 40, 42, the frame connectors 44, the clamps 48, or portions thereof, can be radiographically translucent, such that the fixation system 10, when installed, can allow viewing of a fracture/fusion site of the bone 12 on X-ray film. The radiolucent components or portions thereof can be formed of, for example, carbon, composite, carbon fiber, or other radiolucent materials.

Referring to FIGS. 2, and 3A-3C, various views of the proximal/distal frames 40, 42 are illustrated. It should be appreciated that although identical illustrations are used to show the proximal and distal frames 40, 42, differently sized or shaped frames can also be used. At least one of the proximal and distal frames 40, 42 can have a tri-lobe cross-section defined by three continuous attachment lobes 54 oriented in a three-dimensional configuration, which can be symmetric or non-symmetric. The attachment lobes 54 can provide three separate and spaced-apart continuous attachment surfaces, such that the corresponding proximal or distal frame 40, 42 defines a continuous boundary, at any position of which a frame connector 44 or a frame clamp 48 can be attached. Each lobe 54 can have a substantially curved cross-section, such as a portion of circle or other curve portion. Each of the proximal and distal frames 40, 42 and the associated attachment lobes 54 can be generally U-shaped, although other close or open loop shapes can be used.

Referring to FIGS. 1 and 2, the frame connector 44 can be coupled to the proximal and distal frames 40, 42 using the frame clamps 48 and brackets 56 at each end of the frame connector 44. The brackets 56 can define bores 58 adapted to receive rods 60A and 60B extending from opposite ends of the connectors 44. In one example, the rods 60A and 60B may slidably pass through the respective bores 58 and be securable at a desired location by a set screw 62. Other configurations are contemplated.

The frame clamp 48 can include a jaw opening 70 which can be configured for snap-on clamping on any of the attachment lobes 54 at any position thereon. The frame clamp 48 can also include another opening 72, for receiving any one of various rods, connectors, couplers and adapters for coupling with other fixation components or devices. The opening 72 can also be shaped for constraining rotation having, for example, a D shape.

Figure 4D:
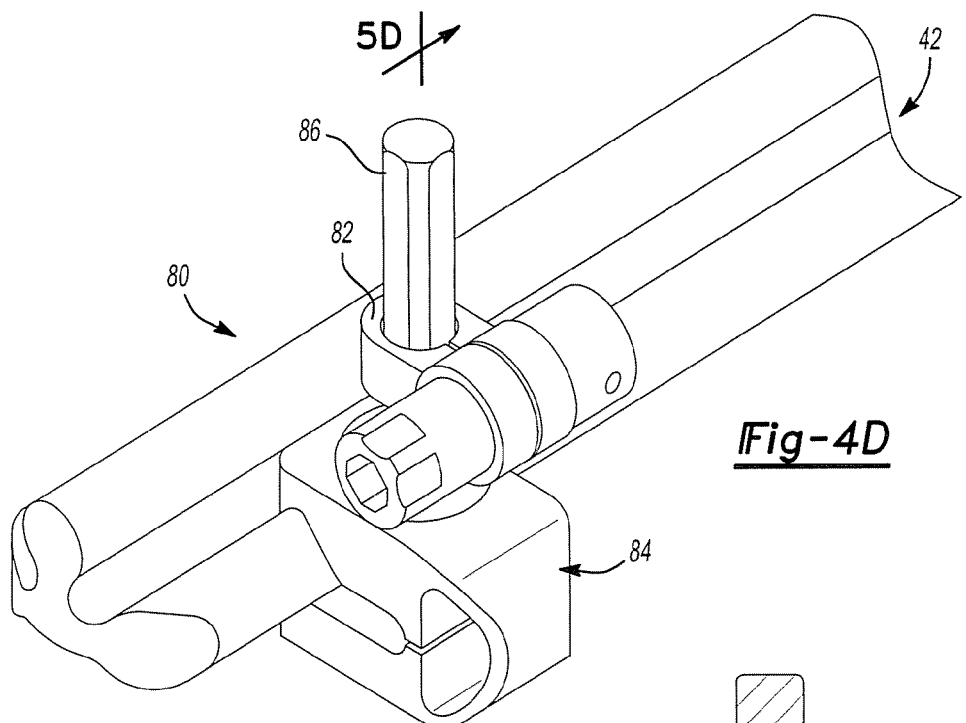
FIG. 4D is a perspective view of a detail of the clamping assembly of FIG. 4A shown coupled with a frame.
Figure 4E:
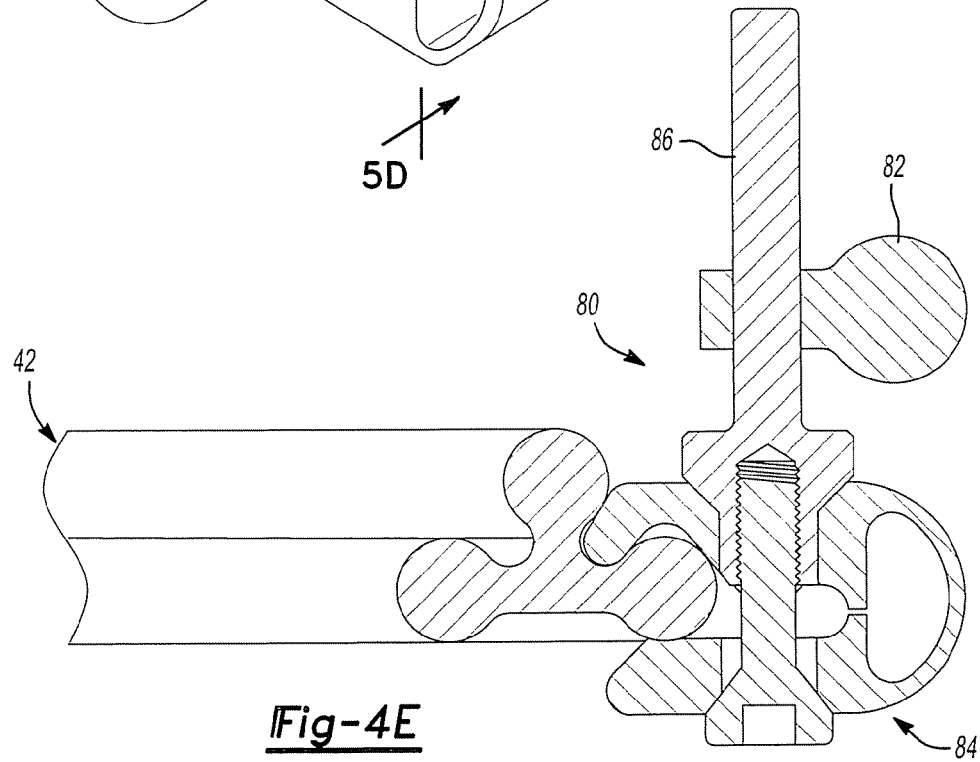
FIG. 4E is a sectional view of the detail shown in FIG. 4D

Referring to FIGS. 4A-4E, an exemplary clamping assembly 80 configured for connecting one of the proximal and distal frames 40, 42 with a fixation wire 50 (shown in FIG. 1) is illustrated. The clamping assembly 80 can include a translational/rotational coupler 82 and one snap-on frame clamp 84 rotatably coupled to a shaft 86. The shaft 86 can be translationally coupled to the translational/rotational coupler 82. Referring to FIG. 4A, adjustability in one translational direction, as indicated by bi-directional arrow $T_1$, and two mutually orthogonal rotational directions, as indicated by curved arrows $R_1$ and $R_2$, can be provided. Detailed views of the clamping assembly 80 at the connection with a distal frame 42 are illustrated in FIGS. 4D and 4E.

Various other clamps or attachment devices may be additionally or alternatively used to couple the frame connectors 44 to the proximal and distal frames 40, 42. Examples of such clamps may be found in commonly owned U.S. patent application entitled "External Fixation System" (Ser. No. 11/297, 745), which is hereby incorporated by reference.

Figure 5A:
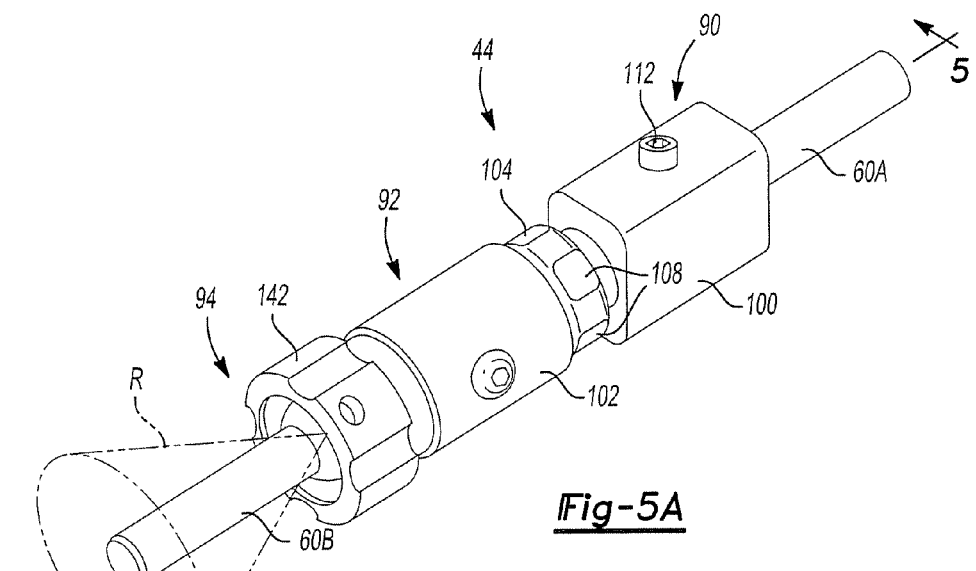
FIG. 5A is a perspective view of a frame connector for an external fixation system according to the present teachings.
Figure 5B:
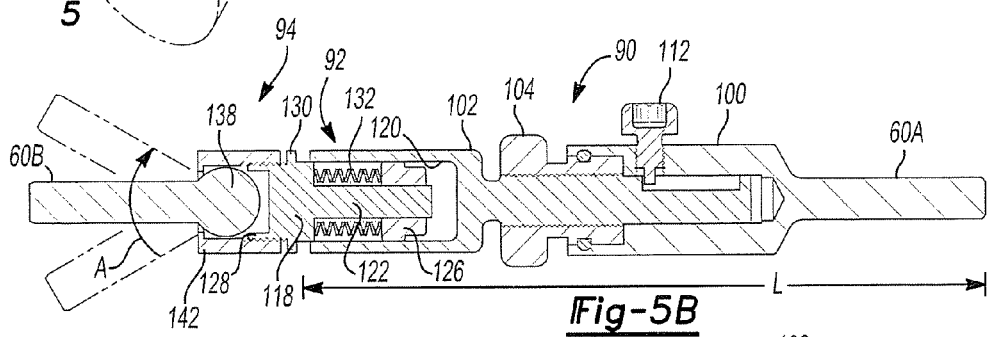
FIG. 5B is a sectional view taken along line 5-5 of the frame connector of FIG. 5A and shown in an unlocked position.
Figure 5C:
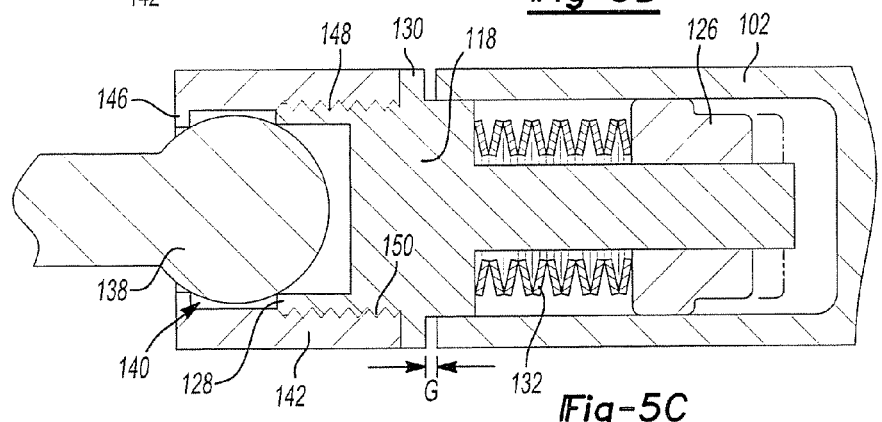
FIG. 5C is a sectional view of the frame connector of FIG. 5 and shown in a locked position.

With reference now to FIGS. 5A, 5B and 5C, the frame connector 44 will be described in greater detail. The frame connector 44 can include a compression/distraction module 90, a dynamization feature 92 and a hinge joint 94.

The compression/distraction module 90 can include first and second members 100, 102 coupled to each other for axial/telescopic motion, which can be controlled by a knob 104, as illustrated in FIG. 5B. The knob 104 can define a radial body having a plurality of planar engagement surfaces 108 (FIG. 5A). The knob 104 can be attached to the first member 100, and can be internally threadably connected to the second member 102. Rotating the knob 104 clockwise or counterclockwise causes relative motion between the first and second members 100, 102, such that the overall length "L" of the compression/distraction module 90 decreases or increases causing contraction/distraction between the structures attached to the rods 60A and 60B of the connector 44. A set screw 112 can be used to maintain a desired magnitude of the length L. In this way, the compression force applied across a fracture/fusion site while the patient is non-load bearing can be adjusted.

The dynamization feature 92 can generally include a third member 118 movable within a cylinder 120 defined by the second member 102. The third member 118 can define a longitudinal member 122 extending between a piston 126 at a first end and a neck 128 at an opposite end. The neck 128 can include a flange 130 extending annularly therefrom. A plurality of disk washers 132 can be stacked in an array around the longitudinal member 122 between the piston 126 and the neck 128. The dynamization feature 92 can be adapted to provide micro-motion at a fracture/fusion site. Explained further, the third member 118 can be adapted to move axially toward and away from the second member 102 thereby altering a gap G (FIG. 5C) defined between the second member 102 and the flange 130 of the third member 118. The disk washers 132 can provide a predetermined biasing force between the respective second and third members 102 and 118.

With particular reference now to FIGS. 5B and 5C, the hinge joint 94 will be described in greater detail. The hinge joint 94 can include a ball 138 and a socket 140. The ball 138 can be formed at a terminal end of the rod 60B. The socket 140 can be defined by a ring 142 and an end of the third member 118. The ring 142 can define an annular shoulder 146 at a first end and threads 148 on a second end. The threads 148 of the ring 142 can be adapted to mate with threads 150 formed on the third member 118. According to one example, the hinge joint 94 can be movable between an unlocked position (FIG. 5B) and a locked position (FIG. 5C). In the unlocked position, the ring 142 can be threadably retracted a distance away from the third member 118 (i.e., moved leftward as viewed in FIG. 5B). In the unlocked position, the ball 138 can be free to rotate within the socket 140. In one example, the ball 138 can be free to rotate within the socket 140 such that the rod 60B can move poly-axially through a range of motion R defining a conical area having an angle A. The angle A can define a range of motion of about 60 degrees through a cross-section of the range of motion R (FIG. 5B).

In the locked position (FIG. 5C), the ring 142 can be threadably advanced a distance toward the third member 118 (i.e., moved rightward as viewed in FIG. 5B). In the locked position, the ball 138 can be securably pinched between the shoulder 146 of the ring 142 and the end of the third member 118. As such, in the locked position, the hinge joint 94 can be precluded from moving.

Figure 6:
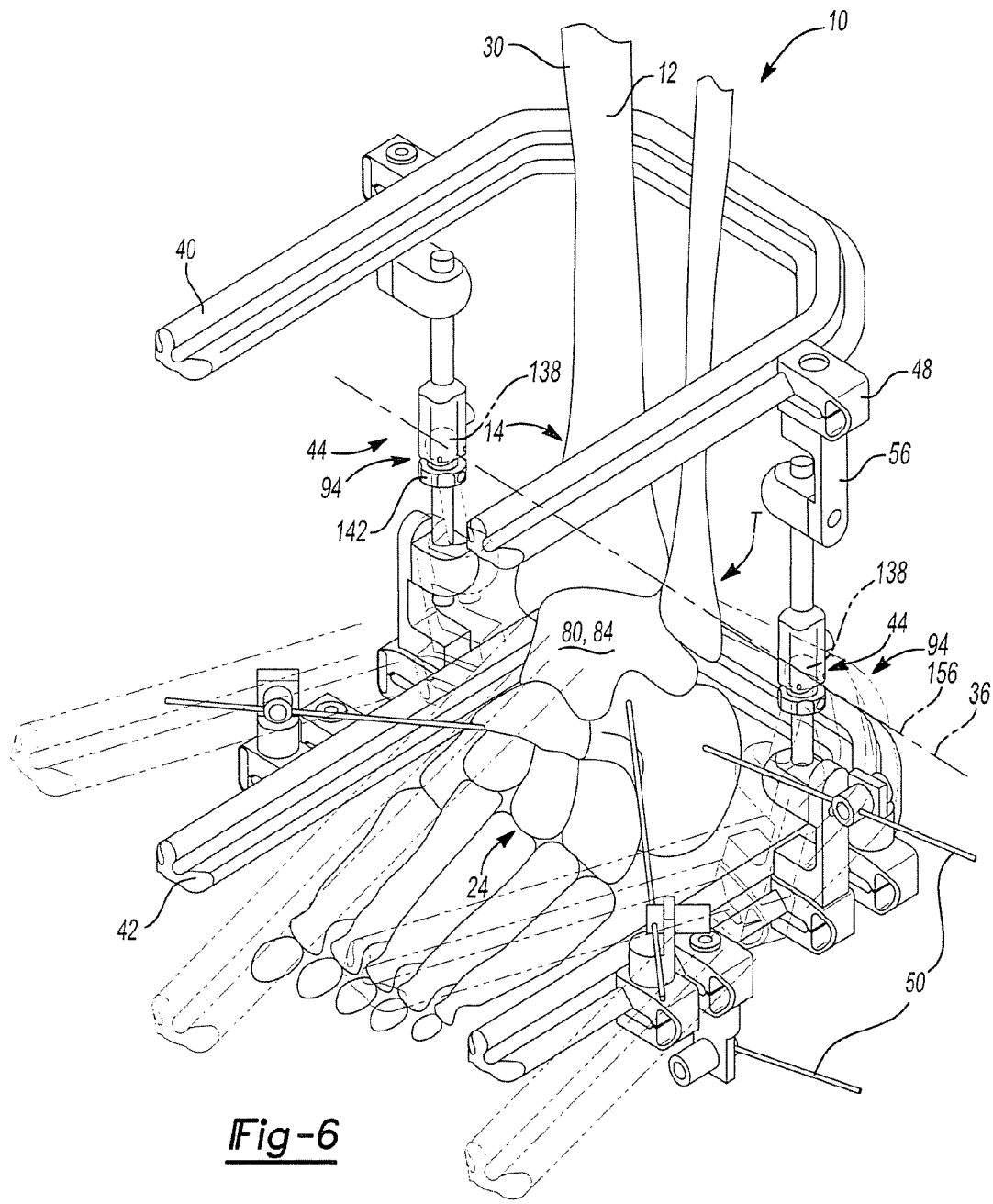
FIG. 6 is a perspective view of the external fixation system of FIG. 1 shown with the connectors pivoting about a pivot joint and permitting movement of the foot about a medial/lateral axis through the ankle.

Turning now to FIG. 6, an exemplary configuration and method of using the fixation system 10 will be described. In general, a pair of connectors 44 can be positioned on opposite sides of the ankle 14, one medially and the other laterally. The connectors 44 can be positioned such that an axis 156 extending through the respective balls 138 passes along the medial/lateral axis 36 through the true ankle joint T. By locating a pair of connectors 44 on opposing medial and lateral positions of the ankle 14, the fixation system 10 can mimic the true anatomical motion of the ankle 14. As can be appreciated, the adjustability of the various clamps 48 and brackets 56 facilitate positioning of the connectors 44 at a desired location on the frames 40, 42. When the hinge joint 94 is in the unlocked position, the foot 24 can be permitted to move up and down at the true ankle joint T about the medial/lateral axis 36. If it is desirable to fix the ankle 14, the respective rings 142 can be advanced to lock the hinge joints 94.

Again, while the preceding discussion is specifically directed toward rotation about the medial/lateral axis 36 defined through the true ankle joint T of an ankle 14, it is appreciated that the connectors 44 and associated hinge joints 94 can be adapted for application elsewhere on the anatomy. Furthermore, as described, the connectors 44 can be adapted to rotate poly-axially. As a result, the fixation system 10 is not limited to controlling motion only around a single axis. In this way, the fixation system 10 may be easily adapted to control motion about other single axes or a plurality of axes concurrently.

The compression/distraction modules 90 of the connectors 44 can transmit a constant compressive force of a desired magnitude to the fracture/fusion site using the actuation knob 104, as discussed above, under non-load bearing use. In addition, the dynamization features 92 can provide micro-motion to the fracture/fusion site.

The foregoing discussion discloses and describes merely exemplary arrangements of the present disclosure. One skilled in the art will readily recognize from such discussion, and from the accompanying drawings and claims, that various changes, modifications and variations can be made therein without departing from the spirit and scope of the disclosure as defined in the following claims. For example, while each of the respective connectors 44 are described as being interconnected between both of the respective frames 40 and 42, it is contemplated that alternatively, one or both of the connectors may be only connected to one frame 40 and 42.

What is claimed is:

1. An external fixation system for a joint having a first bone and a second bone and an anatomical axis of rotation comprising:
   a proximal frame couplable to the first bone;
   a distal frame couplable to the second bone;
   a first connector having a first member pivotally coupled to a second member at a first ball and socket connection, the first member being rotatable through a conical range of motion provided by the first ball and socket connection; and
   a second connector having a third member pivotally coupled to a fourth member at a second ball and socket connection, the third member being rotatable through a conical range of motion provided by the second ball and socket connection;
   wherein the first and second connectors are mountable between the proximal and distal frames at a location such that the anatomical axis of rotation intersects both of the first and second ball and socket connections.

2. The external fixation system of claim 1 wherein at least one of the first and second connectors is adjustably secured at a plurality of locations between the proximal and distal frames.

3. The external fixation system of claim 1 wherein at least one of the first and second connectors is adjustable in a direction toward and away from the proximal frame.

4. The external fixation system of claim 3 wherein at least one of the first and second connectors is adjustable in a direction lateral to the proximal frame.

5. The external fixation system of claim 1 wherein the first member is pivotable relative to the second member through about 60 degrees of motion and the third member is pivotably relative to the fourth member through about 60 degrees of motion.

6. The external fixation system of claim 1 wherein each of the first and second connectors further comprises a ring movable between a locked position wherein the respective ball is fixed relative to the respective socket and an unlocked position wherein the respective ball is free to rotate within the respective socket.

7. The external fixation system of claim 6 wherein each ring is threadably connected to the respective socket.

8. The external fixation system of claim 1 wherein the first connector further comprises a first clamp configured for snap-on attachment at any position along at least one of the proximal and distal frames.

9. The external fixation system of claim 8 wherein the first connector further comprises a second clamp configured for snap-on attachment at any position along the other of the proximal and distal frames.

10. The external fixation system of claim 1 wherein the anatomical axis of rotation is a medial/lateral axis through an ankle joint.

11. The external fixation system of claim 1 wherein at least one of the proximal and distal frames comprises three substantially coextensive and continuous attachment lobes and wherein at least one of the first and second connectors are selectively connected to at least one lobe of the attachment lobes.

12. An external fixation system for a joint having a first bone and a second bone and defining an anatomical axis of rotation comprising:
    a proximal frame selectively attachable to the first bone;
    a distal frame selectively attachable to the second bone, wherein at least one of the proximal and distal frames comprises three substantially coextensive and continuous lobes;
    a first connector selectively connected to at least one lobe of the three substantially coextensive and continuous lobes, the first connector having a first pivot joint; and
    a second connector selectively connected to at least one of the proximal and distal frames and having a second pivot joint;
    wherein the first and second pivot joints are aligned on the anatomical axis of rotation such that one of the first and second bones can rotate about the anatomical axis of rotation relative to the other of the first and second bones.

13. The external fixation system of claim 12 wherein at least one of the first and second connectors is adjustably secured at a plurality of locations between the proximal and distal frames.

14. The external fixation system of claim 12 wherein the first and second connectors each comprises a mechanism for adjusting the magnitude of the compressive force to the bone.

15. The external fixation system of claim 12 wherein both of the proximal and distal frames comprises three substantially coextensive and continuous attachment lobes.

16. The external fixation system of claim 15, further comprising at least one clamp coupled to the connector and structurally configured for snap coupling onto any of the attachment lobes.

17. The external fixation system of claim 12 wherein the anatomical axis of rotation is a medial/lateral axis through an ankle joint.

18. The external fixation system of claim 12 wherein the first pivot joint includes a first ball that rotates within a first socket such that a first rod extending from the first ball and connected to one of the proximal and distal frames moves poly-axially, and wherein the second pivot joint includes a second ball that rotates within a second socket such that a second rod extending from the second ball and connected to one of the proximal and distal frames moves poly-axially.

19. The external fixation system of claim 18 wherein the first and second rods both rotate around a conical range of motion.

20. An external fixation system for a joint having a first and second bone and an anatomical axis of rotation comprising:
   a first member couplable to the first bone;
   a second member couplable to the second bone;
   a first pivotable connector connected to the first member and having a first ball and socket joint;
   a second pivotable connector connected to the second member and having a second ball and socket joint; and
   wherein both of the first and second connectors define a poly-axial range of motion about the first and second balls, respectively, and the first and second connectors are positionable such that an anatomical axis of rotation of the joint passes through both of the first and second balls.

21. The external fixation system of claim 20 wherein at least one of the first and second members comprises three substantially coextensive and continuous attachment lobes and wherein the first and second connectors are both connected between the first and second members, at least one of the first and second connectors being coupled to a lobe of the three attachment lobes.

22. The external fixation system of claim 20 wherein at least one of the first and second connectors are adjustable between the first and second members at a plurality of locations.

* * * * *